United States Patent [19]

Keller et al.

[11] Patent Number: 5,306,635
[45] Date of Patent: Apr. 26, 1994

[54] DNA ENCODING IMMUNOGENIC GPIII GLYCOPROTEIN OF VARICELLA ZOSTER VIRUS

[75] Inventors: Paul M. Keller, Lansdale; Mark W. Riemen, Doylestown; Ronald W. Ellis, Overbrook Hills, all of Pa.; Andrew J. Davison, Glasgow, Scotland; Robert S. Lowe, Harleysville, Pa.

[73] Assignee: Merck & Co., Inc., Rahway, N.J.

[21] Appl. No.: 896,038

[22] Filed: Jun. 9, 1992

Related U.S. Application Data

[60] Continuation of Ser. No. 526,075, May 18, 1990, abandoned, which is a division of Ser. No. 859,159, May 2, 1986, Pat. No. 4,952,674.

[51] Int. Cl.$^5$ .................. C12N 15/38; C12N 5/10; C12N 1/19; C12N 1/21
[52] U.S. Cl. .................. 435/240.2; 536/23.72; 435/252.3; 435/252.31; 435/252.33; 435/254.11; 435/254.21; 435/320.1
[58] Field of Search .................. 536/23.72; 435/320.1, 435/69.1, 69.3, 252.3, 240.2, 254, 254.11, 254.21, 252.31, 252.33; 935/9, 12, 32, 70, 71, 72

[56] References Cited

U.S. PATENT DOCUMENTS 4,665,159  5/1987  Dobkin .................. 530/389.4
4,686,101  8/1987  Ellis et al. .................. 424/88

FOREIGN PATENT DOCUMENTS 0211756 of 0000 European Pat. Off. ...... C07K 15/41

OTHER PUBLICATIONS

Chem. Ab. #17, vol. 106, p. 143, Apr. 27, 1987.
Chem. Ab. vol. 106, #21, p. 162, (1987).
Nucleic Acids Research, vol. 14, #10, pp. 4281-4291, (1986).
Proc. Natl. Acad. Sci. vol. 79, pp. 156-160 (1982).
Chem. Ab. vol. 101, #21, p. 574, (1984).
Infect. Immun. vol. 40, pp. 381-388 (1983).
Chem. Ab. vol. 102, #17, p. 148 (1985).
Chem. Ab. vol. 100, #17 135218, (1984).
Keller, et al., Chem. Abstr. vol. 101, No. 189532 (1984).
Merrifield, Science 232: 341-347 (1986).
Welling et al., FEBS 2820 188 No. 2, pp. 215-218 (1985).
Keller et al., J. Virol., vol. 52, No. 1, pp. 293-297 (Oct. 1984).
Ellis et al., J. Virol., vol. 53, pp. 81-88 (1985).
Pouwells, et al., Cloning Vectors pp. VIII-B-a-i-1 to VIII-B-a-i-6, (1985).
Fredrichs et al., J. Virol. 49 pp. 992-996 (1984).
Suggs., Proc. Natl. Acad. Sci. USA 78 pp. 6613-6617 (1981).
Kikuchi, et al., J. Virol. 52, pp. 806-815 (1984).
Davison, et al., J. Virol. 57, pp. 1195-1197 (1986).

Primary Examiner—Richard A. Schwartz
Assistant Examiner—Mary E. Mosher
Attorney, Agent, or Firm—Gerard H. Bencen; Jack L. Tribble; Paul D. Matukaitis

[57] ABSTRACT

A gene of varicella-zoster virus (VZV) which encodes immunogenic outer surface viral proteins has been identified by DNA sequence analysis. Antibodies directed against peptides imputed from the DNA sequence can react with the glycoprotein, which itself is reactive with neutralizing antibodies. The amino-terminal sequence of the purified glycoprotein is identical to a portion of the amino acid sequence imputed from the DNA sequence. This glycoprotein is useful for the preparation of a vaccine against VZV.

4 Claims, No Drawings

DNA ENCODING IMMUNOGENIC GPIII GLYCOPROTEIN OF VARICELLA ZOSTER VIRUS

This is a continuation of application Ser. No. 07/526,075, filed May 18, 1990, now abandoned, which is a division of application Ser. No. 859,159, filed May 2, 1986, now U.S. Pat. No. 4,952,674.

BACKGROUND OF THE INVENTION

Chickenpox is caused by varicella-zoster virus (VZV), a member of the herpesvirus group. The disease occurs in persons with no prior VZV immunity. VZV-specific antibodies can be demonstrated shortly after onset of disease, decline during convalescence, but remain detectable for many years and correlate with immunity to the disease. Chickenpox is highly contagious; over 90% of the population becomes exposed to VZV before they are 20 years old. In most, if not all, cases, VZV apparently becomes latent in dorsal root ganglion cells. From this latent state, VZV can reactivate and cause zoster even in the presence of specific antibodies, probably as a result of weakened cellular immunity. The disease is highly morbid to the immunosuppressed and to those beyond the second decade.

VZV has five major glycoproteins on its surface: gp115 [115 kilodalton (kD) glycoprotein], gp105, gp92, gp83, gp55. These glycoproteins apparently are the products of three genes: gpIII (gp105), gpII (gp115, in the nonreduced state, composed of the reduced species gp62 and gp57), and gpI (gp92, gp83, gp55). Formerly, these genes were referred to as gA, gB, and gC, respectively. Monoclonal (McAb) and polyclonal monospecific antibodies to gA and gB display complement-independent neutralization, and such antibodies to gC display complement-dependent neutralization of VZV.

SUMMARY OF THE INVENTION

A gene of VZV which encodes the immunogenic outer surface viral glycoprotein gpIII has been identified by DNA sequence analysis. Antibodies directed against peptides imputed from the DNA sequence can react with the gpIII glycoprotein which itself is the target of neutralizing antibodies. The amino-terminal sequence of purified gpIII is identical to a portion of the amino acid sequence imputed from the DNA sequence. This glycoprotein is useful for the preparation of a vaccine for VZV.

OBJECTS OF THE INVENTION

It is an object of the present invention to provide antigens which will prevent diseases associated with VZV infections. Another object is to provide antigens which can be used diagnostically to detect antibodies to VZV. Another object is to provide methods for the preparation of these antigens. Another object is to provide methods for using the antigens to raise antibodies to VZV. Another object is to describe the full sequence of protein antigens, which will include peptide antigens, which may be synthesized by other means or expressed in expression vectors. These and other objects of the present invention will be apparent from the following description.

DETAILED DESCRIPTION OF THE INVENTION

The present invention is directed to the identification of that VZV DNA segment which encodes the protective immunogenic gpIII glycoprotein. More specifically, it is directed to a 2.5 kilobase pair (kbp) DNA fragment whose respective nucleotide sequence (and derived amino acid sequence) has been located within the known sequence of the entire VZV genome. The present invention also is directed to vectors containing all or part of this 2.5 kbp DNA fragment. The invention also is directed to host cells which contain these vectors and which cells are capable of expressing all or part of the polypeptide encoded by the 2.5 kbp fragment. In accordance with known techniques, it will be obvious to those skilled in the art that parts of the foregoing polypeptide can be synthesized chemically or modified and still retain immunogenicity. Therefore, the present invention also is directed toward chemical synthesis of domains of this protein, especially domains including and surrounding hydrophilic regions and threonine or serine and asparagine-X-serine or asparagine-X-threonine residues, wherein X is any amino acid residue, since these domains are likely to reside on the outer surface of the virus.

The DNA segment which encodes gpIII is identified precisely as follows By use of immune-affinity chromatography mediated by McAb to VZV gpIII, the gpIII polypeptide is purified to 90% homogeneity. This preparation, when inoculated into guinea pigs in complete Freund's adjuvant, is capable of eliciting the production of neutralizing antibodies. This purified preparation is electrophoresed by preparative sodium dodecyl sulfatepolyacrylamide gel electrophoresis (SDS-PAGE) and isolated on polybrene-coated glass-fiber sheets as a single 105 kD polypeptide. This sample is subjected to amino-terminal sequence analysis. Based upon a run of 7 consecutive amino acids resolved in the analysis, a pool of oligonulceotides representing every possible coding combination for the heptapeptide is synthesized. The oligonucleotide pool is radiolabelled for use as a hybridization probe to VZV DNA fragments. Specific hybridization is found to a domain within the HindIII B fragment. DNA sequence analysis of this region of HindIII B reveals a 2.5 kbp open reading frame (ORF). Within the amino acid sequence imputed from this DNA sequence, residues 18-27 form a perfect match with the amino-terminal sequence described above. Based on the imputed amino acid sequence, 3 peptides of lengths 13-22 residues are selected as likely to be immunogenic. These peptides are synthesized, coupled to bovine serum albumin, and injected into rabbits. Some of the anti-peptide sera are reactive with gpIII by Western blot analysis and by immunoprecipitation analysis. Further specificity of the anti-peptide serum is shown by the ability of anti-peptide antibodies to compete with McAb to gpIII in immunoprecipitation analysis. In addition, the anti-peptide antibodies can immunoprecipitate an 80 kD in vitro translational product of mRNA hybrid selected by the 2.5 kbp ORF.

In accordance with known techniques, it will be obvious to those skilled in the art that all or part of the above-mentioned DNA fragment can be placed into an expression vector system in order to produce all or part of the protective immunogenic polypeptide. Such an expression vector system often consists of a plasmid which is inserted into a prokaryotic or eukaryotic cell in order to direct expression of a foreign polypeptide. Such a plasmid usually contains sequences for selection of host cells containing the plasmid, amplification of plasmid copy number within the host cell, initiation of transcription of the gene for the foreign polypeptide, termination of transcription of the gene for the foreign polypeptide, in addition to the coding sequence per se which specifies the foreign polypeptide. Therefore, the present invention also is directed to host cells and vectors containing all or part of the 2.5 kbp DNA fragment. Examples of suitable host cells for expression of VZV proteins include prokaryotic cells, such as *E. coli* and *B. subtillis*, and eukaryotic cells, such as *S. cerevisiae* and continuous mammalian cell lines including but not limited to Chinese Hamster Ovary cells and Vero cells.

These proteins are useful individually or in combination when placed in a physiologically acceptable carrier, e.g., saline or phosphate buffered saline, to elicit neutralizing antibodies against VZV disease when administered to a member of a mammalian species, e.g., quinea pigs, in an amount of approximately 5 to 150 mcg per dose, preferably from approximately 10 to 50 mcg per dose. One or more doses may be administered to produce effective protection against VZV disease. The protein may be administered by injection, e.g., subcutaneously or intramuscularly. It is also to be understood that these proteins can be expressed directly in humans by means of appropriate viral expression vectors such as adeno, vaccinia, or herpes simplex.

The following examples illustrate the present invention without, however, limiting the same thereto. The disclosure of each reference mentioned in the following examples is hereby incorporated by reference.

EXAMPLE I

Purification of VZV gpIII Glycoprotein

Ascites fluids, carrying McAb A1 (described in Keller et al., J. Virology 52: 293, 1984), were harvested from mice. An equal volume of 0.15M NaCl was added. Then, a saturated $(NH_4)_2SO_4$ solution was added in an equal total volume and held at 4° C. overnight. This mixture was centrifuged at 10° C. and 2000 rpm. The pellet was resuspended in distilled $H_2O$ (2 mg/ml) and dialyzed overnight against coupling buffer (0.1M $NaHCO_3$, 0.5M NaCl, pH 8.4). One gram of cyanogen bromide-activated Sepharose 4B (Pharmacia, Piscataway, N.J.) was swollen in 0.001N HCl, then decanted into a 60 ml coarse sintered glass funnel. This was washed with 200 ml 0.001N HCl, then 50 ml coupling buffer. The Sepharose then was mixed with 10 ml of McAb solution and rotated for 2 hours at 23° C. Then, 80 μl ethanolamine was added and the solution was rotated for 1 hour at 23° C. The resin was poured into a disposable chromatography column (BioRad), drained and washed successively with 10 ml volumes of the following solutions: 1) coupling buffer; 2) 0.1M $Na_2HPO_4$; 0.5M NaCl, pH 8.2; 3) 0.1M NaOAc, 0.5M NaCl, pH 4.0; 4) 0.1M $NaHBO_4$, pH 8.2; 5) 3M KSCN; 6) 0.1M $NaHBO_4$, pH 8.2. Then it is stored in 0.1M $NaHBO_4$, pH 8.2 at 4° C. prior to use.

VZV glycoproteins were purified form MRC-5 human diploid fibroblasts which were infected with VZV to the extent of 80% cytopathic effect. Cells in 750 cm² roller bottles were washed twice with 0.15M NaCl, 0.01M $Na_2HPO_4$, pH 7.2 and drained well. Ten ml of 50 mM Tris, pH 7.5, 2% Triton X-100, 4 mM phenylmethylsulfonylfluoride (PMSF) were incubated 15 minutes to the bottle while rolling. The same 10 ml then were used successively to extract 9 more roller bottles. A fresh 10 ml aliquot of buffer was used successively to rinse the 10 roller bottles and pooled with the first aliquot, such that 20 ml of extract represent material from 10 roller bottles. Extracts were stored at −70° C. until use. Extracts were thawed and dialyzed overnight at 4° C. against 0.15M NaCl, 0.01M $Na_2HPO_4$, 0.05% Triton X-100, pH 7.2, then clarified by centrifuging at 1500 rpm for 15 minutes at 4° C. Extract (20 ml) was added to 1 g of McAb-coupled resin and incubated overnight at 4° C. with shaking. The slurry was centrifuged for 15 minutes at 1500 rpm at 4° C. and washed three times with 0.1M $NaHBO_4$, pH 8.2. The glycoprotein was eluted by incubation at 23° C. with 10 ml 3M KSCN. The eluate immediately was dialyzed against 0.15M NaCl, 0.01M $Na_2HPO_4$, 0.05% Triton X-100, pH 7.2 overnight at 4° C. and concentrated to approximately 1 mg/ml.

This peak was verified as VZV gpIII by the following criteria. In silver stains of SDS-PAGE run under reducing conditions, the sample was resolved as one polypeptide species of molecular weight 105 kD as described in Keller et al., ibid., i.e., gp105; Shiraki et al., J. Gen. Virology 61: 255 (1982), i.e., gPl; Grose et al., Inf. Immun. 40: 381 (1983), i.e., gp118, Forghani et al., J. Virology 52: 55 (1984), i.e., 118K. In addition, a parallel aliquot of [$^{35}$S]-methioninelabelled cell extract purified by the technique could be immunoprecipitated specifically with McAb to gpIII, resulting in the resolution by SDS-PAGE of a single 105 kD species.

EXAMPLE II

Purified VZV gpIII polypeptide induces antibodies which neutralize VZV infectivity in vitro Guinea pigs were inoculated intramuscularly with 20 micrograms in complete Freund's adjuvant of VZV gpIII (purified by immune-affinity chromatography as described above in Example I), followed one month later by two inoculations each of ten micrograms of VZV gpIII in incomplete Freund's adjuvant spaced two weeks apart. Sera were obtained from the guinea pigs after these three inoculations. Each of the guinea pig sera was utilized in an in vitro VZV neutralization assay as described (Keller et al., ibid.). By this assay, the post-immunization, but not the pre-immunization sera, contained VZV-neutralizing antibodies.

EXAMPLE III

N-Terminal amino acid sequence of purified VZV qpIII polypeptide

200 μg of VZV gpIII, prepared as described in Example I, were electrophoresed by preparative SDS-PAGE (7.5% polyacrylamide) and isolated on polybrene-coated glass-fiber sheets as a single polypeptide of 105 kD [van de Kerckhove et al., Eur. J. Biochem. 152: 9 (1985)]. This sample was subjected to amino-terminal sequence analysis using an Applied Biosystems Gas-Phase Sequenator [Hewick et al., J. Biol. Chem. 256: 7790 (1981)]. The phenylthiohydantoin amino acids produced at each step were separated and quantitated by high performance liquid chromatography [Speiss et al., Proc. Nat. Acad. Sci. U.S.A. 70: 2974 (1979)]. The sequence analysis demonstrated that gpIII contains a single unblocked amino-terminus. As shown in Table I, this sequence (with 2 gaps) can be aligned perfectly with amino acids 18–27 in Example V (see below) which have been imputed from the DNA sequence of the 2.5 kbp ORF.

TABLE 1

N-Terminal amino acid sequence of purified VZV gpIII

| 1 | asn | lys | ser | tyr | val | thr | pro | thr | pro | ala |

TABLE 1-continued

N-Terminal amino acid sequence of purified VZV gpIII

| 2 | 18 | 19 | 20 | 21 | 22 | 23 | 24 | 25 | 26 | 27 |
|---|---|---|---|---|---|---|---|---|---|---|
| 3 | — | lys | ser | tyr | val | thr | pro | thr | — | ala |

1 = imputed amino acids from Example V.
2 = amino acid position in the ORF of sequence 1.
3 = amino acid sequence of purified VZV gpIII, wherein a dash (—) means that no amino acid was resolved at that position in the analysis.

EXAMPLE IV

Use of oligonucleotides based on amino acid sequence data to identify the gpIII gene Based on the N-terminal amino acid sequence of gpIII, derived as described in Example III and presented in Table 1, a pool of oligonucleotides was designed which represents every possible combination of DNA sequences capable of encoding this amino acid sequence. This pool is

```
      A   A   C   A   A   A
    AA  TCGTA  GTGACGCCGAC
      G   C   T   C   C   C
          T       T   T   T
``` and

```
      A   C   C   A   A   A
    AA  AG  TA  GTGACGCCGAC
      G   T   T   C   C   C
                  T   T   T
``` lys—ser—tyr—val—thr—pro—thr (amino acid residues 19-25)

These oligonucleotide pools were labelled with [32P] ATP in the presence of T4 polynucleotide kinase. The probe was hybridized to a Southern blot of HindIII fragments of VZV. By this analysis, the above gene sequence was localized to the HindIII B fragment.

EXAMPLE V

Determination of nucleotide sequences of the 2.5 kbp segment of VZV DNA

The complete nucleotide sequence of the VZV HindIII-B DNA segment contains several large ORFs. One of these ORFs is 2.5 kbp in length, encodes a 90 kD protein, and contains a DNA sequence (Example IV) which codes for the amino terminal gpIII sequence in Example III. The nucleotide sequence for the complete 2.5 kbp segment which encodes the gpIII glycoprotein is given below:

ATG TTT GCG CTA GTT TTA GCG GTG GTA ATT CTT
GTA ACA CCA ACC CCT GCG ACT CGC TCT ATC GGA

CCT CTT TGG ACC ACG GCT AAT AAA TCT TAC
CAT ATG TCT GCT CTT CTA CGA GAA TAT TCC

GAC CGT AAT ATG TCT CTG AAA TTA GAA GCC TTT
AAA TCA CTT CAC TGG GGA AAT GAT AGA AAA CAC

TAT CCT ACT GGT TTC GAT GAA GAA CTC ATT
GTT TTC TTG GTT ATT GTT AAG GTT AAC CCT

ACA ACA CAC GAA GGA GAC GTC GGG CTG GTT ATA
TTC AAA GCA GAA CAT CGA GCA CCG TTT CCT GCT

TTT CCA AAA TAC TTG TTA TCG CCA TAC CAT
GGA CGT TTT GGA TTT CTT AGT CAC CCT GTG

ACA CCC GAC GTG AGC TTC TTT GAC AGT TCG TTT
GCG TTT ACT ACG TTC CCA CCA AAC CCC CTT GTA

-continued

GCG CCG TAT TTA ACT ACG CAA CAT CTT GTT
TGG CAT TTG GAA AGA GCT GAG ACC GCA GCA

ACT GCA GAA AGG CCG TTT GGG GTA AGT CTT TTA
ATT CTG GAA CAT AAA GCG CAT TTT GCT ACA TGG

CCC GCT CGC CCA ACA GTC CCC AAG AAT ACT
GAT GCC CTT GCC CGA CAT ACT TTT TTT TCT

GCC GAA GCA ATT ATC ACC AAC TCA ACT TTG AGA
CCA ATT CGA TAC TGG GCC ACC GGT TCG GTG CTT

ATA CAC GTT CCC CTT TTT GGG TCG GTA TGG
CTC ACA AGC GAC TCG GGT CGT GTG GAA GTA

AAT ATT GGT GTA GGA TTT ATG AGC TCG CTC ATT
ATT GTT GTA CCA CAT ACA GTA AAA CTG AAC GCG

TCT TTA TCC TCT GGA CCA CCG ATA GAA TTA
GTT ACA AGC GAC ACC ACA TGG TTC CAG CTA

AAT CCA CCG GGT CCG GAT CCG GGG CCA TCT TAT
ATG AAT TTT TCA AAG CAT GCT ACG GTC GAT ATA

CGA GTT TAT TTA CTT GGA CGT GGG TTG GAT
TGC GCA TAT CCC GAA GAG AGT TTG GAT TAC

CGC TAT CAT TTA TCC ATG GCC CAC ACG GAG GCT
GAC ATA AAC GAG GAA AGC TAT TAC CAT ATC GCC

CTG CGG ATG ACA ACG AAG GCG GAT CAA CAT
GCA AGA ATA GCC ACA TCA ATT TTT GCG TTG

TCG GAA ATG GGC CGT ACC ACA GAA TAT TTT CTG
TTA AAA TTC CTT AAT TAC ATT TTA ATG CGG ATA

TTA GAT GAG ATC GTA GAT GTT CAG TAT CAA
GGA GCA GGA GCT CAT CCC AAC ACT ATA TCC

GGA ACC TCG GAT CTG ATC TTT GCC GAT CCA TCG
GGT CAG GTA AAA CCC GCA AAT GTC GAT TAT TTT

CAG CTT CAT GAC GAA CTT TCA CTT CTT TTT
ATT TCA TAT GAT GAA GCC CGT GAT CAA CTA

AAG ACC GCA TAC GCG CTT TCC CGT GGT CAA GAC
GTT ATA ATG AGC ATA TAC AAG GGG CTG CTT GTG

CAT GTG AAT GCA CCT TCT CTC GCC AGG CGT
AAG CAA AAT TTA AAT GCT ACA GAG AGG CAG

GCT TTA TTT TTT GCC TCA ATG ATT TTA TTA AAT
GTA TTA GAC GGT CGC ACA ACT TTG CTT TTA ATG

TTC CGC GAA GGA CTA GAA AAT TCA TCT CGG
ACA TCC ATG TGT ACG GCA GCT CAC GCC ACG

CAA GCA GCA CTT AAC ATA CAA GAA GGC CTG GCA
ATA CCA AAC GTA TAC AGT CCT TGT ATG GGT TCC

TAC TTA AAT CCT TCA AAA CAC ATG TTT ACA
CTT CGT ACA GAC CTC ACG GAA GAG ATT CAT

GTT ATG AAT CTC CTG TCG GCA ATA CCA ACA CGC
CTA GAC GAA TCT GAA ATA TTC GAC GCG GCA TTT

CCA GGA CTT AAC GAG GTA TTG CAT ACC CAA
AAA ACC ATG ATG ATT TTT ACC ACA TGG ACT

GCC AAA GAT TTG CAT ATA CTC CAC ACC CAT GTA
GCG CGT AAC GGA GAA TAT GTG CTC ATT CTT CCA

CCA GAA GTA TTT ACG TGT CAA GAT GCA GCC
GCT GTC CAG GGA CAC AGT TAT GTG ATT ACA

CGA AAC AAA CCT CAA AGG GGT TTG GTA TAT TCC
TCC GTT GTT TAT TTA AGC AGG GAT ACT TGC GTG

CTG GCA GAT GTG GAT GTA TAT AAC CCC ATA
TCT GAA CAT GGT GTC ATA GAG ACG GTC GCA

-continued
```
CTG CCC CAT CCG GAC AAT TTA AAA GAA TGT TTG
ACC ACG GGG GCG ATT ATG GAT ATA ATT ATT ATT

TAT TGC GGA AGT GTT TTT CTT AGG TAT CTA
GAC AGC AAA GAT ACA GAA CGA CAA CTA GCC

GCT ATG GGA AAC TCC ACA ATT CCA CCC TTC AAT
GTG TTG TTG TTT CCA AAC GGA ACT GTG GTA ACG

CCA GAC ATG CAC GGG GAT GAC TCT AAG GCT
CTT CTA GGA TTC GAA CGA CGA CAA GCC
```

-continued
```
ATA CGA ATG TCG GGA CAA TAC CTT GGG GCC TCT
TTT GGT ATT ATC GGA TGG ATG TTA TGT GGA AAT

TTA GGA GGG GCG TTT CTG GCG GTA GTG GGG
TCC CGC CTT CGA GAA TAT AAT AAA ATA CCT

CTG ACA TAA
```

The foregoing nucleotide sequences encode the following peptide:

```
                                               10                              20
         Met Phe Ala Leu Val Leu Ala Val Val Ile Leu Pro Leu Trp Thr Thr Ala Asn Lys Ser
                                               30                              40
         Tyr Val Thr Pro Thr Pro Ala Thr Arg Ser Ile Gly His Met Ser Ala Leu Leu Arg Glu
                                               50                              60
         Tyr Ser Asp Arg Asn Met Ser Leu Lys Leu Glu Ala Phe Tyr Pro Thr Gly Phe Asp Glu
                                               70                              80
         Glu Leu Ile Lys Ser Leu His Trp Gly Asn Asp Arg Lys His Val Phe Leu Val Ile Val
                                               90                             100
         Lys Val Asn Pro Thr Thr His Glu Gly Asp Val Gly Leu Val Ile Phe Pro Lys Tyr Leu
                                              110                             120
         Leu Ser Pro Tyr His Phe Lys Ala Glu His Arg Ala Pro Phe Pro Ala Gly Arg Phe Gly
                                              130                             140
         Phe Leu Ser His Pro Val Thr Pro Asp Val Ser Phe Phe Asp Ser Ser Phe Ala Pro Tyr
                                              150                             160
         Leu Thr Thr Gln His Leu Val Ala Phe Thr Thr Phe Pro Pro Asn Pro Leu Val Trp His
                                              170                             180
         Leu Glu Arg Ala Glu Thr Ala Ala Thr Ala Glu Arg Pro Phe Gly Val Ser Leu Leu Pro
                                              190                             200
         Ala Arg Pro Thr Val Pro Lys Asn Thr Ile Leu Glu His Lys Ala His Phe Ala Thr Trp
                                              210                             220
         Asp Ala Leu Ala Arg His Thr Phe Phe Ser Ala Glu Ala Ile Ile Thr Asn Ser Thr Leu
                                              230                             240
         Arg Ile His Val Pro Leu Phe Gly Ser Val Trp Pro Ile Arg Tyr Trp Ala Thr Gly Ser
                                              250                             260
         Val Leu Leu Thr Ser Asp Ser Gly Arg Val Glu Val Asn Ile Gly Val Gly Phe Met Ser
                                              270                             280
         Ser Leu Ile Ser Leu Ser Ser Gly Pro Pro Ile Glu Leu Ile Val Val Pro His Thr Val
                                              290                             300
         Lys Leu Asn Ala Val Thr Ser Asp Thr Thr Trp Phe Gln Leu Asn Pro Pro Gly Pro Asp
                                              310                             320
         Pro Gly Pro Ser Tyr Arg Val Tyr Leu Leu Gly Arg Gly Leu Asp Met Asn Phe Ser Lys
                                              330                             340
         His Ala Thr Val Asp Ile Cys Ala Tyr Pro Glu Glu Ser Leu Asp Tyr Arg Tyr His Leu
                                              350                             360
         Ser Met Ala His Thr Glu Ala Leu Arg Met Thr Thr Lys Ala Asp Gln His Asp Ile Asn
                                              370                             380
         Glu Glu Ser Tyr Tyr His Ile Ala Ala Arg Ile Ala Thr Ser Ile Phe Ala Leu Ser Glu
                                              390                             400
         Met Gly Arg Thr Thr Glu Tyr Phe Leu Leu Asp Glu Ile Val Asp Val Gln Tyr Gln Leu
                                              410                             420
         Lys Phe Leu Asn Tyr Ile Leu Met Arg Ile Gly Ala Gly Ala His Pro Asn Thr Ile Ser
                                              430                             440
         Gly Thr Ser Asp Leu Ile Phe Ala Asp Pro Ser Gln Leu His Asp Glu Leu Ser Leu Leu
                                              450                             460
         Phe Gly Gln Val Lys Pro Ala Asn Val Asp Tyr Phe Ile Ser Tyr Asp Glu Ala Arg Asp
                                              470                             480
         Gln Leu Lys Thr Ala Tyr Ala Leu Ser Arg Gly Gln Asp His Val Asn Ala Leu Ser Leu
                                              490                             500
         Ala Arg Arg Val Ile Met Ser Ile Tyr Lys Gly Leu Leu Val Lys Gln Asn Leu Asn Ala
                                              510                             520
         Thr Glu Arg Gln Ala Leu Phe Phe Ala Ser Met Ile Leu Leu Asn Phe Arg Glu Gly Leu
                                              530                             540
         Glu Asn Ser Ser Arg Val Leu Asp Gly Arg Thr Thr Leu Leu Leu Met Thr Ser Met Cys
                                              550                             560
         Thr Ala Ala His Ala Thr Gln Ala Ala Leu Asn Ile Gln Glu Gly Leu Ala Tyr Leu Asn
                                              570                             580
         Pro Ser Lys His Met Phe Thr Ile Pro Asn Val Tyr Ser Pro Cys Met Gly Ser Leu Arg
                                              590                             600
         Thr Asp Leu Thr Glu Glu Ile His Val Met Asn Leu Leu Ser Ala Ile Pro Thr Arg Pro
                                              610                             620
         Gly Leu Asn Glu Val Leu His Thr Gln Leu Asp Glu Ser Glu Ile Phe Asp Ala Ala Phe
                                              630                             640
         Lys Thr Met Met Ile Phe Thr Thr Trp Thr Ala Lys Asp Leu His Ile Leu His Thr His
                                              650                             660
         Val Pro Glu Val Phe Thr Cys Gln Asp Ala Ala Ala Arg Asn Gly Glu Tyr Val Leu Ile
                                              670                             680
         Leu Pro Ala Val Gln Gly His Ser Tyr Val Ile Thr Arg Asn Lys Pro Gln Arg Gly Leu
```

-continued

```
                                        690                                              700
Val Tyr Ser Leu Ala Asp Val Asp Val Tyr Asn Pro Ile Ser Val Val Tyr Leu Ser Arg
                                            710                                          720
Asp Thr Cys Val Ser Glu His Gly Val Ile Glu Thr Val Ala Leu Pro His Pro Asp Asn
                                        730                                              740
Leu Lys Glu Cys Leu Tyr Cys Gly Ser Val Phe Leu Arg Tyr Leu Thr Thr Gly Ala Ile
                                        750                                              760
Met Asp Ile Ile Ile Ile Asp Ser Lys Asp Thr Glu Arg Gln Leu Ala Ala Met Gly Asn
                                            770                                          780
Ser Thr Ile Pro Pro Phe Asn Pro Asp Met His Gly Asp Asp Ser Lys Ala Val Leu Leu
                                        790                                              800
Phe Pro Asn Gly Thr Val Val Thr Leu Leu Gly Phe Glu Arg Arg Gln Ala Ile Arg Met
                                            810                                          820
Ser Gly Gln Tyr Leu Gly Ala Ser Leu Gly Gly Ala Phe Leu Ala Val Val Gly Phe Gly
                                        830                                              840
Ile Ile Gly Trp Met Leu Cys Gly Asn Ser Arg Leu Arg Glu Tyr Asn Lys Ile Pro Leu
                                            850                                          860
Thr
```

EXAMPLE VI

Based on the DNA sequence of Example V and its imputed amino acid sequence, 3 domains were chosen for the synthesis of peptides which would be likely to elicit the production of antibodies against gpIII. These domains are: 1) phe$^{152}$-pro$^{173}$ (22-mer), 2) glu$^{793}$-tyr$^{804}$ (12-mer), and 3) gly$^{828}$-thr$^{841}$ (14 mer). The first 2 were obtained from Peninsula Laboratories Inc. The latter was synthesized on an Applied Biosystems Inc. 430A solid-phase peptide synthesizer. All synthetic peptides, with an amino-terminal acetyl group and a carboxy-terminal hydroxyl group, were characterized by reversed-phase high performance liquid chromatography and amino acid analysis. Each peptide was conjugated to bovine serum albumin according to established techniques [Walter et al., Proc. Natl. Acad. Sci. USA 77:5197 (1980); Gutkowska et al., Biochem Biophys. Res. Commun. 122:593 (1984)]. A quantity, 5–10 mg/1.0 ml, of each conjugate was injected into rabbits intramuscularly in complete Freund's adjuvant at week 0 and in incomplete Freund's adjuvant at week 4. Rabbits were bled at week 8. Sera were utilized in Western blot analysis at 1:500 dilutions. The antisera recognized a 105 kD polypeptide. In immunoprecipitation analyses, 1:30 dilutions of sera that were incubated with [$^{35}$S] methionine-labelled infected cell extracts immunoprecipitated a 105 kD polypeptide. The 105 kD species was conclusively demonstrated to be gpIII by virtue of the ability of McAb to gpIII (A1 in Keller et al., ibid.), but not McAb to gpI or gpII (C5 and B1, respectively in Keller et al., ibid.), to preclear the 105 kD polypeptide from the lysate by 2 successive immunoprecipitations, as shown by abrogation of the immunoprecipitability of the 105 kD polypeptide by the anti-peptide sera.

EXAMPLE VII

The 2.5 kbp DNA ORF can select RNA encoding the precursor protein to gpIII

Cystoplasmic RNA was prepared from VZV-infected MRC-5 cells as described (Chirgwin et al., Biochemistry 18 5294 (1979). The RNA encoded by the 2.5 kbp ORF in the VZV HindTTT B fragment as well as nonselected RNA and RNA selected by other fragments were selected by hybridization to cloned VZV DNA fragments [Ecker & Hyman, Proc. Natl Acad. Sci. USA 79:156 (1982)] bound to nitrocellulose [Cooper et al., J. Virology 37: 284 (1981)]. These RNAs were translated in a rabbit reticulocyte lysate. The polypeptide products were immunoprecipitated by one polyclonal monospecific rabbit antibody raised to the synthetic peptide described in Example VI. By this analysis, it was found that an 80 kD in vitro translational product from mRNA selected by the 2.5 kbp ORF in the VZV HindIII-B fragment could be immunoprecipitated by the anti-peptide sera.

What is claimed is:

1. A 2.5 kbp fragment of VZV DNA having the nucleotide sequence:

```
ATG TTT GCG CTA GTT TTA GCG GTG GTA ATT CTT
GTA ACA CCA ACC CCT GCG ACT CGC TCT ATC GGA

CCT CTT TGG ACC ACG GCT AAT AAA TCT TAC
CAT ATG TCT GCT CTT CTA CGA GAA TAT TCC

GAC CGT AAT ATG TCT CTG AAA TTA GAA GCC TTT
AAA TCA CTT CAC TGG GGA AAT GAT AGA AAA CAC

TAT CCT ACT GGT TTC GAT GAA GAA CTC ATT
GTT TTC TTG GTT ATT GTT AAG GTT AAC CCT

ACA ACA CAC GAA GGA GAC GTC GGG CTG GTT ATA
TTC AAA GCA GAA CAT CGA GCA CCG TTT CCT GCT

TTT CCA AAA TAC TTG TTA TCG CCA TAC CAT
GGA CGT TTT GGA TTT CTT AGT CAC CCT GTG

ACA CCC GAC GTG AGC TTC TTT GAC AGT TCG TTT
GCG TTT ACT ACG TTC CCA CCA AAC CCC CTT GTA

GCG CCG TAT TTA ACT ACG CAA CAT CTT GTT
TGG CAT TTG GAA AGA GCT GAG ACC GCA GCA

ACT GCA GAA AGG CCG TTT GGG GTA AGT CTT TTA
ATT CTG GAA CAT AAA GCG CAT TTT GCT ACA TGG

CCC GCT CGC CCA ACA GTC CCC AAG AAT ACT
GAT GCC CTT GCC CGA CAT ACT TTT TTT TCT

GCC GAA GCA ATT ATC ACC AAC TCA ACT TTG AGA
CCA ATT CGA TAC TGG GCC ACC GGT TCG GTG CTT

ATA CAC GTT CCC CTT TTT GGG TCG GTA TGG
CTC ACA AGC GAC TCG GGT CGT GTG GAA GTA

AAT ATT GGT GTA GGA TTT ATG AGC TCG CTC ATT
ATT GTT GTA CCA CAT ACA GTA AAA CTG AAC GCG

TCT TTA TCC TCT GGA CCA CCG ATA GAA TTA
GTT ACA AGC GAC ACC ACA TGG TTC CAG CTA

AAT CCA CCG GGT CCG GAT CCG GGG CCA TCT TAT
ATG AAT TTT TCA AAG CAT GCT ACG GTC GAT ATA

CGA GTT TAT TTA CTT GGA CGT GGG TTG GAT
TGC GCA TAT CCC GAA GAG AGT TTG GAT TAC

CGC TAT CAT TTA TCC ATG GCC CAC ACG GAG GCT
GAC ATA AAC GAG GAA AGC TAT TAC CAT ATC GCC
```

-continued

CTG CGG ATG ACA ACG AAG GCG GAT CAA CAT
GCA AGA ATA GCC ACA TCA ATT TTT GCG TTG

TCG GAA ATG GGC CGT ACC ACA GAA TAT TTT CTG
TTA AAA TTC CTT AAT TAC ATT TTA ATG CGG ATA

TTA GAT GAG ATC GTA GAT GTT CAG TAT CAA
GGA GCA GGA GCT CAT CCC AAC ACT ATA TCC

GGA ACC TCG GAT CTG ATC TTT GCC GAT CCA TCG
GGT CAG GTA AAA CCC GCA AAT GTC GAT TAT TTT

CAG CTT CAT GAC GAA CTT TCA CTT CTT TTT
ATT TCA TAT GAT GAA GCC CGT GAT CAA CTA

AAG ACC GCA TAC GCG CTT TCC CGT GGT CAA GAC
GTT ATA ATG AGC ATA TAC AAG GGG CTG CTT GTG

CAT GTG AAT GCA CCT TCT CTC GCC AGG CGT
AAG CAA AAT TTA AAT GCT ACA GAG AGG CAG

GCT TTA TTT TTT GCC TCA ATG ATT TTA TTA AAT
GTA TTA GAC GGT CGC ACA ACT TTG CTT TTA ATG

TTC CGC GAA GGA CTA GAA AAT TCA TCT CGG
ACA TCC ATG TGT ACG GCA GCT CAC GCC ACG

CAA GCA GCA CTT AAC ATA CAA GAA GGC CTG GCA
ATA CCA AAC GTA TAC AGT CCT TGT ATG GGT TCC

TAC TTA AAT CCT TCA AAA CAC ATG TTT ACA
CTT CGT ACA GAC CTC ACG GAA GAG ATT CAT

GTT ATG AAT CTC CTG TCG GCA ATA CCA ACA CGC
CTA GAC GAA TCT GAA ATA TTC GAC GCG GCA TTT

CCA GGA CTT AAC GAG GTA TTG CAT ACC CAA
AAA ACC ATG ATG ATT TTT ACC ACA TGG ACT

GCC AAA GAT TTG CAT ATA CTC CAC ACC CAT GTA
GCG CGT AAC GGA GAA TAT GTG CTC ATT CTT CCA

CCA GAA GTA TTT ACG TGT CAA GAT GCA GCC
GCT GTC CAG GGA CAC AGT TAT GTG ATT ACA

CGA AAC AAA CCT CAA AGG GGT TTG GTA TAT TCC
TCC GTT GTT TAT TTA AGC AGG GAT ACT TGC GTG

CTG GCA GAT GTG GAT GTA TAT AAC CCC ATA
TCT GAA CAT GGT GTC ATA GAG ACG GTC GCA

CTG CCC CAT CCG GAC AAT TTA AAA GAA TGT TTG
ACC ACG GGG GCG ATT ATG GAT ATA ATT ATT ATT

TAT TGC GGA AGT GTT TTT CTT AGG TAT CTA
GAC AGC AAA GAT ACA GAA CGA CAA CTA GCC

GCT ATG GGA AAC TCC ACA ATT CCA CCC TTC AAT
GTG TTG TTG TTT CCA AAC GGA ACT GTG GTA ACG

CCA GAC ATG CAC GGG GAT GAC TCT AAG GCT
CTT CTA GGA TTC GAA CGA CGA CAA GCC

ATA CGA ATG TCG GGA CAA TAC CTT GGG GCC TCT
TTT GGT ATT ATC GGA TGG ATG TTA TGT GGA AAT

TTA GGA GGG GCG TTT CTG GCG GTA GTG GGG
TCC CGC CTT CGA GAA TAT AAT AAA ATA CCT

CTG ACA TAA or a subportion of the foregoing sequence encoding an immunogenic epitope selected from the group consisting of phe[152]-pro[173]; glu[793]-tyr[804]; and gly[828]-thr[841].

2. An expression vector containing all or part of the 2.5 kbp DNA fragment having the nucleotide sequence.

ATG TTT GCG CTA GTT TTA GCG GTG GTA ATT CTT
GTA ACA CCA ACC CCT GCG ACT CGC TCT ATC GGA

-continued

CCT CTT TGG ACC ACG GCT AAT AAA TCT TAC
CAT ATG TCT GCT CTT CTA CGA GAA TAT TCC

GAC CGT AAT ATG TCT CTG AAA TTA GAA GCC TTT
AAA TCA CTT CAC TGG GGA AAT GAT AGA AAA CAC

TAT CCT ACT GGT TTC GAT GAA GAA CTC ATT
GTT TTC TTG GTT ATT GTT AAG GTT AAC CCT

ACA ACA CAC GAA GGA GAC GTC GGG CTG GTT ATA
TTC AAA GCA GAA CAT CGA GCA CCG TTT CCT GCT

TTT CCA AAA TAC TTG TTA TCG CCA TAC CAT
GGA CGT TTT GGA TTT CTT AGT CAC CCT GTG

ACA CCC GAC GTG AGC TTC TTT GAC AGT TCG TTT
GCG TTT ACT ACG TTC CCA CCA AAC CCC CTT GTA

GCG CCG TAT TTA ACT ACG CAA CAT CTT GTT
TGG CAT TTG GAA AGA GCT GAG ACC GCA GCA

ACT GCA GAA AGG CCG TTT GGG GTA AGT CTT TTA
ATT CTG GAA CAT AAA GCG CAT TTT GCT ACA TGG

CCC GCT CGC CCA ACA GTC CCC AAG AAT ACT
GAT GCC CTT GCC CGA CAT ACT TTT TTT TCT

GCC GAA GCA ATT ATC ACC AAC TCA ACT TTG AGA
CCA ATT CGA TAC TGG GCC ACC GGT TCG GTG CTT

ATA CAC GTT CCC CTT TTT GGG TCG GTA TGG
CTC ACA AGC GAC TCG GGT CGT GTG GAA GTA

AAT ATT GGT GTA GGA TTT ATG AGC TCG CTC ATT
ATT GTT GTA CCA CAT ACA GTA AAA CTG AAC GCG

TCT TTA TCC TCT GGA CCA CCG ATA GAA TTA
GTT ACA AGC GAC ACC ACA TGG TTC CAG CTA

AAT CCA CCG GGT CCG GAT CCG GGG CCA TCT TAT
ATG AAT TTT TCA AAG CAT GCT ACG GTC GAT ATA

CGA GTT TAT TTA CTT GGA CGT GGG TTG GAT
TGC GCA TAT CCC GAA GAG AGT TTG GAT TAC

CGC TAT CAT TTA TCC ATG GCC CAC ACG GAG GCT
GAC ATA AAC GAG GAA AGC TAT TAC CAT ATC GCC

CTG CGG ATG ACA ACG AAG GCG GAT CAA CAT
GCA AGA ATA GCC ACA TCA ATT TTT GCG TTG

TCG GAA ATG GGC CGT ACC ACA GAA TAT TTT CTG
TTA AAA TTC CTT AAT TAC ATT TTA ATG CGG ATA

TTA GAT GAG ATC GTA GAT GTT CAG TAT CAA
GGA GCA GGA GCT CAT CCC AAC ACT ATA TCC

GGA ACC TCG GAT CTG ATC TTT GCC GAT CCA TCG
GGT CAG GTA AAA CCC GCA AAT GTC GAT TAT TTT

CAG CTT CAT GAC GAA CTT TCA CTT CTT TTT
ATT TCA TAT GAT GAA GCC CGT GAT CAA CTA

AAG ACC GCA TAC GCG CTT TCC CGT GGT CAA GAC
GTT ATA ATG AGC ATA TAC AAG GGG CTG CTT GTG

CAT GTG AAT GCA CCT TCT CTC GCC AGG CGT
AAG CAA AAT TTA AAT GCT ACA GAG AGG CAG

GCT TTA TTT TTT GCC TCA ATG ATT TTA TTA AAT
GTA TTA GAC GGT CGC ACA ACT TTG CTT TTA ATG

TTC CGC GAA GGA CTA GAA AAT TCA TCT CGG
ACA TCC ATG TGT ACG GCA GCT CAC GCC ACG

CAA GCA GCA CTT AAC ATA CAA GAA GGC CTG GCA
ATA CCA AAC GTA TAC AGT CCT TGT ATG GGT TCC

TAC TTA AAT CCT TCA AAA CAC ATG TTT ACA
CTT CGT ACA GAC CTC ACG GAA GAG ATT CAT

-continued
```
GTT ATG AAT CTC CTG TCG GCA ATA CCA ACA CGC
CTA GAC GAA TCT GAA ATA TTC GAC GCG GCA TTT CCA GGA CTT AAC GAG GTA TTG CAT ACC CAA
    AAA ACC ATG ATG ATT TTT ACC ACA TGG ACT GCC AAA GAT TTG CAT ATA CTC CAC ACC CAT GTA
GCG CGT AAC GGA GAA TAT GTG CTC ATT CTT CCA CCA GAA GTA TTT ACG TGT CAA GAT GCA GCC
    GCT GTC CAG GGA CAC AGT TAT GTG ATT ACA CGA AAC AAA CCT CAA AGG GGT TTG GTA TAT TCC
TCC GTT GTT TAT TTA AGC AGG GAT ACT TGC GTG CTG GCA GAT GTG GAT GTA TAT AAC CCC ATA
    TCT GAA CAT GGT GTC ATA GAG ACG GTC GCA CTG CCC CAT CCG GAC AAT TTA AAA GAA TGT TTG
ACC ACG GGG GCG ATT ATG GAT ATA ATT ATT ATT TAT TGC GGA AGT GTT TTT CTT AGG TAT CTA
    GAC AGC AAA GAT ACA GAA CGA CAA CTA GCC
```

-continued
```
GCT ATG GGA AAC TCC ACA ATT CCA CCC TTC AAT
GTG TTG TTG TTT CCA AAC GGA ACT GTG GTA ACG

CCA GAC ATG CAC GGG GAT GAC TCT AAG GCT
    CTT CTA GGA TTC GAA CGA CGA CAA GCC

ATA CGA ATG TCG GGA CAA TAC CTT GGG GCC TCT
TTT GGT ATT ATC GGA TGG ATG TTA TGT GGA AAT

TTA GGA GGG GCG TTT CTG GCG GTA GTG GGG
    TCC CGC CTT CGA GAA TAT AAT AAA ATA CCT

CTG ACA TAA
```
or a subportion of the foregoing sequence encoding an immunogenic epitope selected from the group consisting of phe$^{152}$-pro$^{173}$; glu$^{793}$-tyr$^{804}$; and gly$^{828}$-thr$^{841}$.

3. A suitable prokaryotic or eukaryotic host cultured cell containing a vector according to claim 2.

4. An expression vector according to claim 2 wherein said sequence is expressed directly in a mammalian species.

* * * * *